United States Patent [19]
Roman

[11] Patent Number: 5,607,301
[45] Date of Patent: Mar. 4, 1997

[54] ORTHODONTIC BRACKET AND METHOD OF MOUNTING

[75] Inventor: Patrick Roman, Escondido, Calif.

[73] Assignee: Lancer Orthodontics, San Marcos, Calif.

[21] Appl. No.: 332,897

[22] Filed: Nov. 1, 1994

[51] Int. Cl.6 .................................................. A61C 3/00
[52] U.S. Cl. ................................................................ 433/8
[58] Field of Search ........................... 433/8, 9, 10, 11, 433/16, 17

[56] References Cited

U.S. PATENT DOCUMENTS

| | | | |
|---|---|---|---|
| 3,922,787 | 12/1975 | Fischer et al. | |
| 4,183,141 | 1/1980 | Dellinger et al. | |
| 4,299,569 | 11/1981 | Frantz | 433/8 |
| 4,337,037 | 6/1982 | Kurz | 433/8 |
| 4,415,330 | 11/1983 | Daisley et al. | 433/16 |
| 4,531,911 | 6/1985 | Creekmore | 433/8 |
| 4,536,154 | 8/1985 | Garton, Jr. et al. | 433/8 |
| 4,659,309 | 4/1987 | Merkel | 433/16 X |
| 4,799,882 | 1/1989 | Kesling | 433/8 |
| 4,819,316 | 4/1989 | Rossini et al. | 433/8 X |
| 5,022,854 | 6/1991 | Broughton et al. | 433/8 |
| 5,030,089 | 7/1991 | Kawaguchi | 433/8 |
| 5,067,897 | 11/1991 | Tuneberg | 433/8 |
| 5,109,586 | 5/1992 | Jones et al. | 29/160.6 |
| 5,123,838 | 6/1992 | Cannon | 433/14 |
| 5,125,831 | 6/1992 | Rospisil | 433/8 |
| 5,161,969 | 11/1992 | Pospisil et al. | 433/8 |
| 5,174,753 | 12/1992 | Wool | 433/8 |
| 5,299,934 | 4/1994 | Suyama | 433/8 |
| 5,302,116 | 4/1994 | Viazis | 433/8 |
| 5,439,379 | 8/1995 | Hansen | 433/8 |

Primary Examiner—Nicholas D. Lucchesi
Attorney, Agent, or Firm—Fulwider Patton Lee & Utecht, LLP

[57] ABSTRACT

An orthodontic bracket is provided to assist in aligning with the occlusal plane in the tooth long axis of a patient's tooth when mounting the bracket on the tooth. The orthodontic bracket has a tie wing recess having a rhomboidal configuration and an archwire slot recess also having a rhomboidal configuration. Vertical sight lines are used to assist in aligning with the tooth long axis and the horizontal sight lines are used to assist in aligning with the occlusal plane. The archwire slot recess also reduces friction between the archwire slot and the archwire.

31 Claims, 5 Drawing Sheets

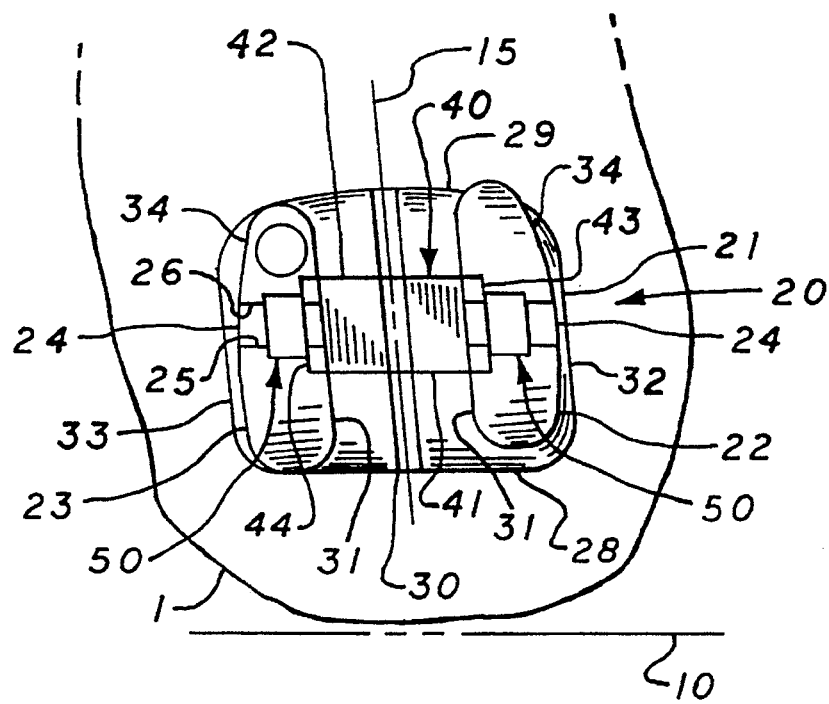
FIG. 4
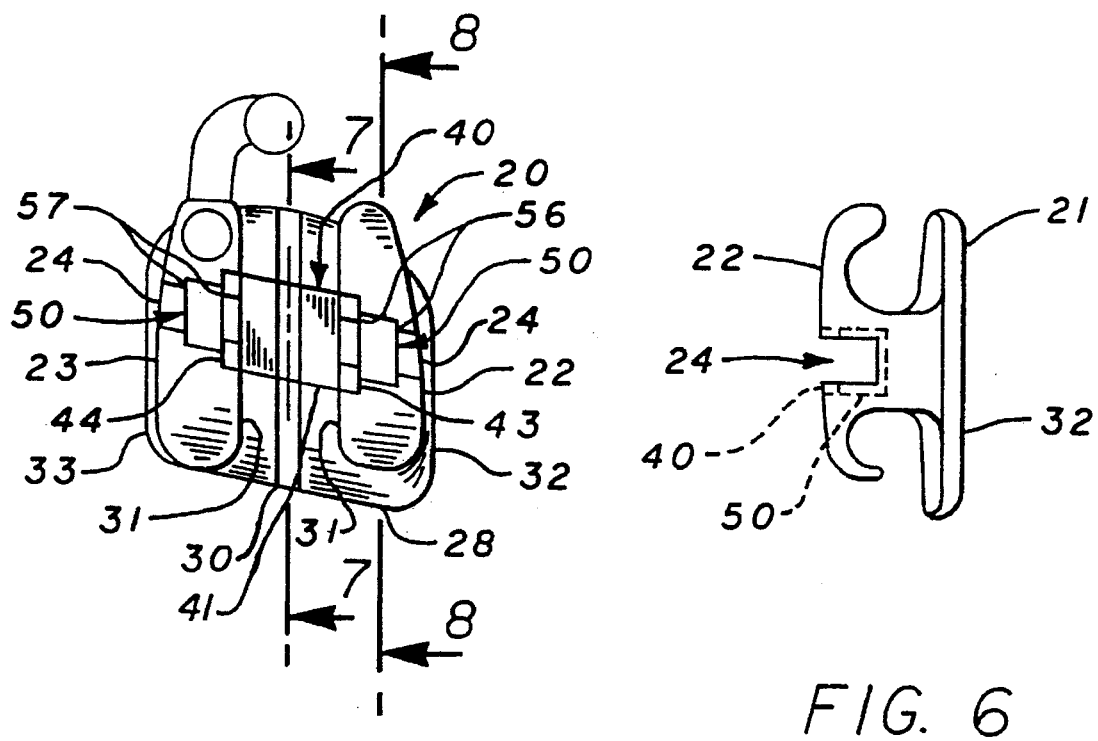
FIG. 5
FIG. 6

ORTHODONTIC BRACKET AND METHOD OF MOUNTING

BACKGROUND OF THE INVENTION

The invention relates generally to the field of orthodontics in which malaligned teeth receive corrective braces to reposition the teeth into proper alignment in the dental arch. More specifically, an orthodontic bracket is provided in which horizontal and vertical sight lines are used to facilitate alignment when the bracket is mounted on a tooth. The invention also is directed to an archwire recess that both facilitates alignment and reduces frictional forces between the archwire and the archwire slot.

As is well known in the art, malaligned teeth can be corrected by moving them into their proper orientation using orthodontic brackets. With the development of better adhesives to bond orthodontic brackets to a tooth, the size of the orthodontic brackets have become smaller and smaller over the past number of years. As a consequence, and because present day adhesives have a tendency to dry rapidly, the amount of time an orthodontist has to place an orthodontic bracket on a patient's tooth, before the adhesive dries, is reduced to a matter of seconds. Coupled with the small size of the orthodontic bracket itself, orthodontists have routinely sought new bracket designs to facilitate alignment of orthodontic brackets on the tooth.

More specifically, orthodontists have sought bracket designs and methods which help align the archwire slot with the occlusal plane of the patient's teeth. A further reference line, although imaginary, is the tooth long axis of the tooth. Thus, the occlusal plane and the tooth long axis are two reference lines which the orthodontist utilizes in mounting a bracket on the tooth.

Some prior art brackets, such as that shown in U.S. Pat. Nos. 3,477,128; 3,660,900; and 3,881,252, depict various orthodontic brackets in which the archwire slot is slanted with respect to the tie wings. By slanting the archwire slot, each orthodontic bracket can be mounted such that the archwire slot of each bracket on each tooth is parallel to the occlusal plane which insures that all of the archwire slots of the various orthodontic brackets will align parallel to the occlusal plane. When the archwire is then fitted into the archwire slot of each bracket, the archwire also will be parallel to the occlusal plane and there will be no need to make any bends in the archwire as was typical of the prior art devices.

A further development in orthodontic bracket design is depicted in U.S. Pat. No. 4,415,330. In this patent, the orthodontic bracket has a pair of tie wings having mesial and distal sides parallel to the tooth long axis which are used to facilitate alignment with the tooth long axis. The bracket also has an archwire slot and tie wing tips that are parallel to each other and parallel to the occlusal plane. Thus, this bracket provides both horizontal and vertical sight lines to facilitate in aligning the bracket on a tooth. Due to its specific configuration, this prior art bracket has an overall rhomboidal shape.

It has been determined that one of the primary reference lines used by the orthodontist in mounting a bracket on a patient's tooth is the occlusal edge of the base pad upon which the tie wings are mounted. The occlusal edge of the base pad is not only the longest edge of the orthodontic bracket, but it is the edge closest to the occlusal plane. Also, it has been found that a groove on the base pad bisecting the tie wings and being parallel to the tie wings, assist the orthodontist in aligning the bracket with the tooth long axis. It has been determined by orthodontists that the groove in the base pad and the inner edges of the tie wings provide the closest sight lines to the imaginary tooth long axis for assisting in aligning the bracket on the tooth. Some prior art brackets have incorporated a groove and a base pad with an occlusal edge parallel to the occlusal plane.

While the prior art brackets provide some assistance to the orthodontist, there remain problems in aligning a bracket due to the small size of the brackets and to fast-drying adhesives. Thus, what has been heretofore desired and unavailable is an orthodontic bracket having further sight lines that are parallel to the occlusal plane and to the tooth long axis which will assist the orthodontist in rapidly and more accurately mounting an orthodontic bracket on a tooth. The present invention provides these characteristics.

SUMMARY OF THE INVENTION

The present invention relates to an orthodontic bracket to assist in aligning with the occlusal plane and the tooth long axis of a patient's tooth. The orthodontic bracket has a mesial tie wing and a distal tie wing separated by a distance and which are attached to a base pad. An archwire slot is disposed in both the mesial tie wing and the distal tie wing such that the archwire slot is parallel to the occlusal plane of a patient's tooth. A tie wing recess is provided in the mesial tie wing and the distal tie wing, the tie wing recess having at least an occlusal edge and a gingival edge parallel to the archwire slot and parallel to the occlusal plane. The tie wing recess also has a mesial edge and a distal edge parallel to the tooth long axis. The tie wing recess has generally an overall configuration of that of a rhomboid. The tie wing recess can be cut or molded into the tie wings which themselves may have an overall configuration of that of a rectangle, rhomboid, or trapezoid. Further, the present invention contemplates a tie wing recess in tie wings of nearly any configuration, including a single tie wing bracket.

The invention also provides an orthodontic bracket having an archwire recess for reducing friction between the archwire and the archwire slot. A rhomboidal-shaped archwire recess is formed in the archwire slot so that there is less metal-to-metal contact between the archwire and the archwire slot. Thus, when there is relative movement between the archwire and the archwire slot, since the metal-to-metal contact has been reduced by the archwire recess, there is less friction and the archwire will slide more easily through the archwire slot. This is particularly important during the beginning of a treatment period when the tooth movement may be at its greatest and the occurrence of friction between the archwire and the archwire slot is the greatest. The archwire recess has an occlusal edge and a gingival edge, both of which are parallel to each other and to the archwire slot and occlusal plane. The occlusal and gingival edges of the archwire recess assist in alignment with the occlusal plane, providing consistent visual cues or sight lines. The archwire recess also has mesial and distal edges that are parallel to each other and parallel to the tooth long axis, again to assist in alignment and to provide consistent visual cues in the alignment process.

Other features and advantages of the present invention will become more apparent from the following detailed description of the invention, when taken in conjunction with the accompanying exemplary drawings.

BRIEF DESCRIPTION OF THE DRAWINGS

FIG. 4 is a front elevational view of an orthodontic bracket of the present invention mounted on a tooth.

FIG. 5 is a front elevational view of an orthodontic bracket similar to FIG. 4 only having a different angulation.

FIG. 6 is a side view of the orthodontic bracket of FIG. 5.

Figure 11:
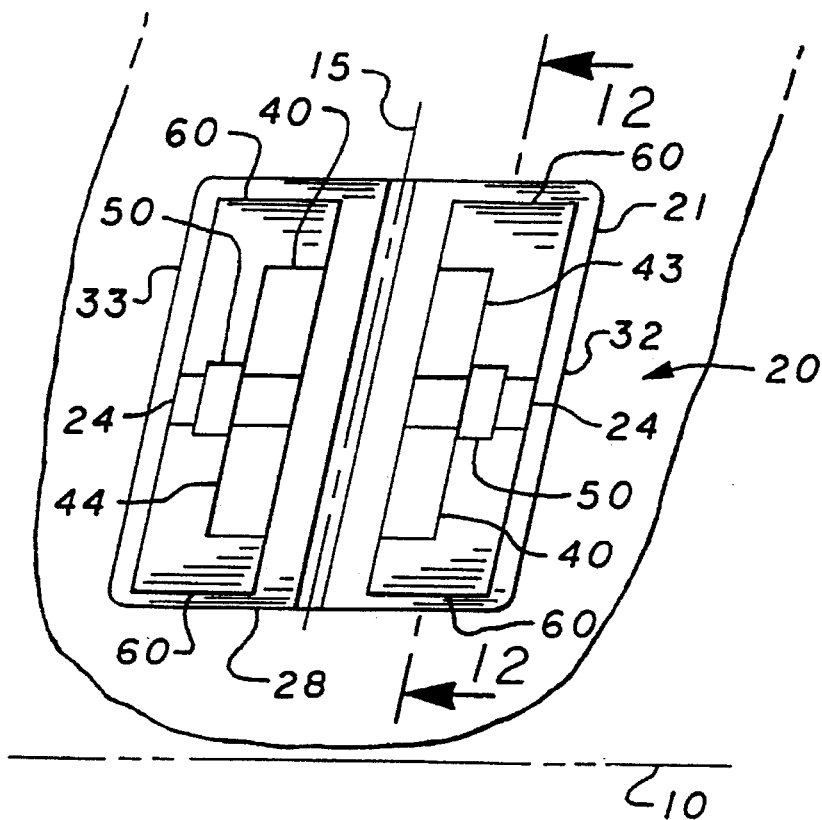
FIG. 11 is a front elevational view of another embodiment of the orthodontic bracket of the present invention.
Figure 12:
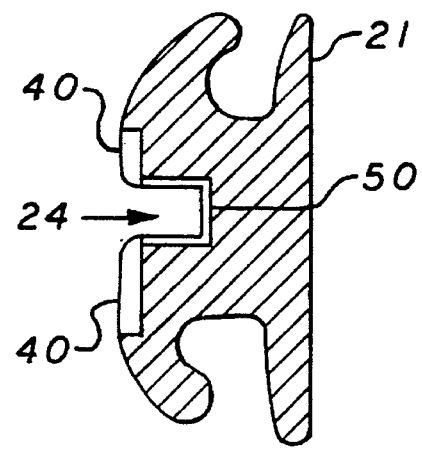

FIG, 12 is a cross-sectional view of the orthodontic bracket of FIG. 11 taken along lines 12—12.

Figure 13:
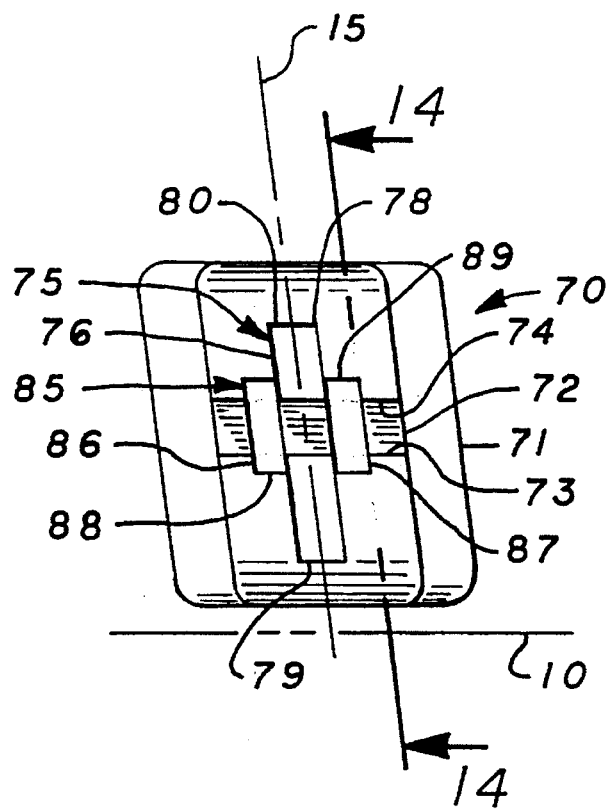

FIG. 13 is a front elevational view of a single wing orthodontic bracket embodying features of the present invention.

Figure 14:
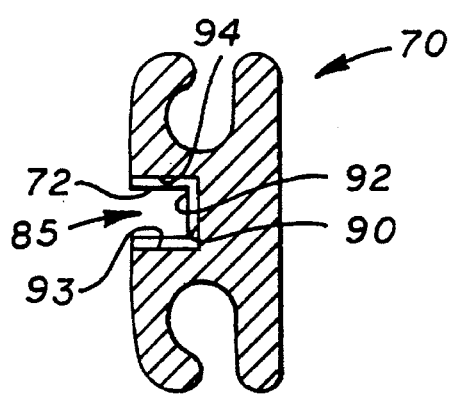

FIG. 14 is a cross-sectional view of the orthodontic bracket of FIG. 13 taken along lines 14—14.

DETAILED DESCRIPTION OF THE PREFERRED EMBODIMENTS

The present invention is directed to orthodontic brackets for use in realigning teeth so that they are properly positioned in the dental arch. Of primary importance are the sight lines or visual cues that the orthodontist uses to assist in aligning the orthodontic bracket with the tooth long axis and the occlusal plane. Like reference numbers used herein refer to like parts.

Figure 1:
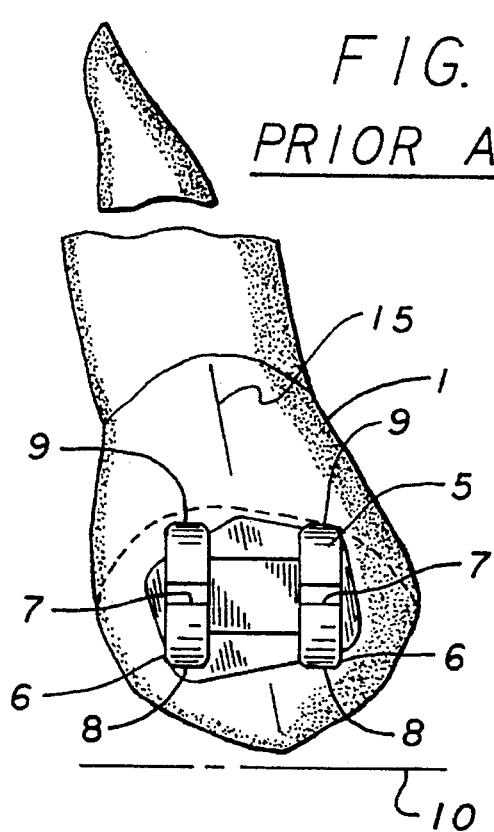
FIG. 1 is a front elevational view of a tooth having a prior art bracket mounted thereon.
Figure 2:
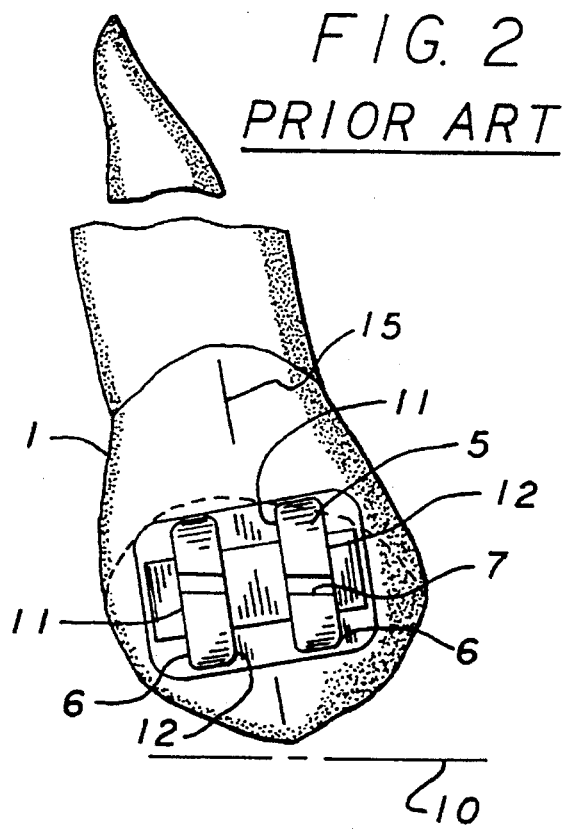
FIG. 2 is a front elevational view of a tooth having a prior art bracket mounted thereon.
Figure 3:
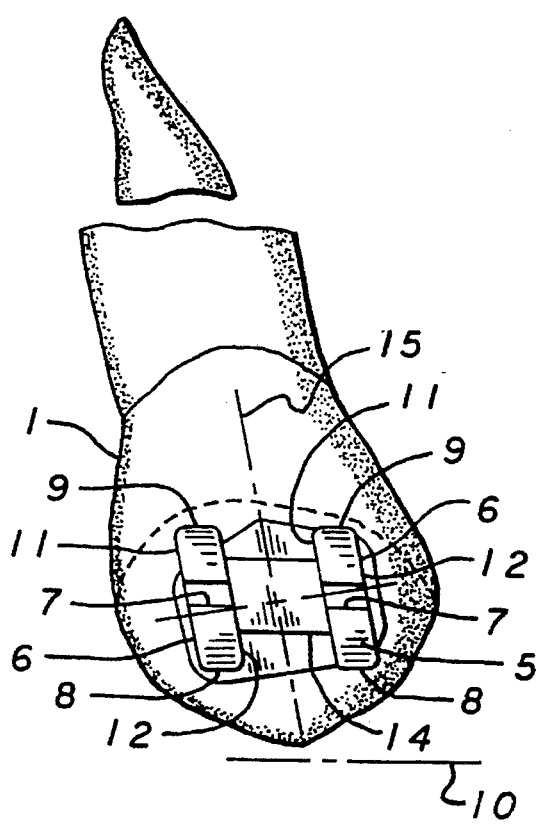
FIG. 3 is a front elevational view of a tooth having a prior art orthodontic bracket mounted thereon.
Figure 7:
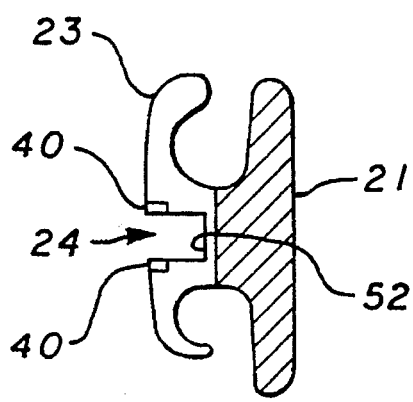
FIG. 7 is a cross-sectional view of the orthodontic bracket of FIG. 5 taken along lines 7—7.
Figure 8:
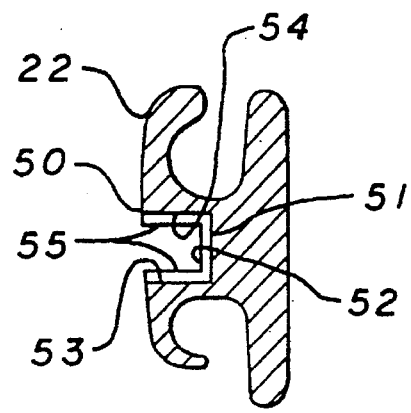
FIG. 8 is a cross-sectional view of the orthodontic bracket of FIG. 5 taken along lines 8—8.

In FIGS. 1–3, the prior art brackets attempted to provide some visual cues that were consistent with aligning with the tooth long axis and the occlusal plane. For example, the prior art bracket depicted in FIG. 1 is mounted on tooth 1 and shows an orthodontic bracket 5 having a pair of tie wings 6 and an archwire slot 7. Each of tie wings 6 have occlusal tie wing tips 8 and gingival tie wing tips 9. As can be seen in FIG. 1, archwire slot 7 and tie wing tips 8, 9 are parallel to each other, and are also parallel to occlusal plane 10. The tooth long axis 15, which essentially bisects the longitudinal axis of the tooth, is generally used as a reference line in aligning the orthodontic bracket. As can be seen in FIG. 1, the mesial and distal edges of tie wings 6 are not parallel to the tooth long axis, and do not assist in aligning the orthodontic bracket with the tooth long axis 15.

Referring to the prior art bracket depicted in FIG. 2, an orthodontic bracket 5 has tie wings 6 which each have mesial sides 11 and distal sides 12. Unlike the FIG. 1 orthodontic bracket, the bracket of FIG. 2 has mesial sides 11 and distal sides 12 of the tie wings parallel to each other and parallel to tooth long axis 15. Thus, the orthodontic bracket is more easily aligned when mounting on the tooth. Archwire slot 7 is parallel to occlusal plane 10, however, the tie wing tips of the bracket in FIG. 2 are not parallel to the occlusal plane, thereby providing inconsistent visual cues for alignment purposes.

The prior art bracket of FIG. 3 has more consistent visual cues in that many of the sight lines are parallel to the tooth long axis and the occlusal plane. Thus, orthodontic bracket 5 has a pair of tie wings 6, each having parallel mesial sides 11 and distal sides 12, which are also parallel to tooth long axis 15. The horizontal visual cues are also consistent in that archwire slot 7 and tie wing tips 8 and 9 are all parallel to each other, and to occlusal plane 10. In addition, a mounting flange 14 has edges which are also parallel to the occlusal plane. Thus, the prior art bracket of FIG. 3 provides more sight lines for alignment purposes than as shown in prior art brackets of FIG. 1 and FIG. 2. As is clear, however, there remains sight lines that can be utilized to further assist in aligning that are not shown in the prior art brackets. The present invention provides these further sight lines making all of the vertical and horizontal lines useable for alignment purposes.

In keeping with the invention, as illustrated in FIGS. 4–8, orthodontic bracket 20 has a mesial tie wing 22 and a distal tie wing 23 which are mounted on or are integral with base pad 21. In other words, base pad 21 may be separately formed from mesial and distal tie wings 22, 23, or they all may be formed as a single unit such as by molding. Base pad 21 is bonded directly to the tooth 1. Orthodontic bracket 20 also has an archwire slot 24 disposed at an angle to the longitudinal axis of mesial and distal tie wings 22, 23. Archwire slot 24 has an occlusal edge 25 and a gingival edge 26 which are parallel to each other and which are parallel to occlusal plane 10. Base pad 21 has an occlusal edge 28 that also is parallel to the archwire slot and parallel to occlusal plane 10. As can be seen, occlusal edge 28 is the longest and closest edge to occlusal plane 10, thus it is important for alignment purposes that occlusal edge 28 be parallel to occlusal plane 10 in order to assist in mounting the bracket on the tooth. Base pad 21 also has gingival edge 29 that, although curved as depicted in FIG. 4, is generally parallel to occlusal edge 28 and occlusal plane 10. Thus, the gingival and occlusal edges of base pad 21 and archwire slot 24 provide consistent visual cues in aligning the bracket on the tooth with reference to occlusal plane 10.

Further referring to FIG. 4, vertical sight lines are provided to assist with alignment along tooth long axis 15. The sight lines closest to the tooth long axis are generally the most useful in aligning the bracket. Thus, groove 30 is provided in base pad 21 such that its sides are parallel to tooth long axis 15, and are spaced only a few millimeters apart, at the most, so that alignment with tooth long axis 15 is more easily accomplished. Tie wings 22, 23 have inner edges 31 which are parallel to each other and parallel to tooth long axis 15 to provide further visual cues for alignment. Additional visual cues are the mesial edge 32 and the distal edge 33 of base pad 21. In the embodiment shown, the mesial and distal edges 32, 33 of the base pad 21 are parallel to each other and to the tooth long axis 15. The outer edges 34 of the tie wings are curved and roughly approximate the anatomical contour of the tooth 1 and in this embodiment do not align with the tooth long axis. These curved outer edges are not parallel to each other nor are they parallel to the tooth long axis.

In further keeping with the invention, a tie wing recess 40 is provided to increase the number of sight lines useable by the orthodontist for aligning the bracket with respect to occlusal plane 10 and tooth long axis 15. Tie wing recess 40 has an occlusal edge 41 and a gingival edge 42 that are parallel to each other and parallel to occlusal plane 10. Tie wing recess 40 also has mesial edge 43 and distal edge 44 that are parallel to each other and parallel to the tooth long axis 15. Thus, the overall shape of tie wing recess is that of a rhomboidal configuration providing further sight lines to assist in aligning the bracket with the occlusal plane and tooth long axis. Tie wing recess 40 is essentially a channel or depression cut or molded into tie wings 22, 23 for a distance, but not deep enough so as to impair the structural integrity of the tie wings. In the embodiment shown, the wing recess 40 overlies the archwire slot 24.

Further with respect to the invention, as depicted in FIGS. 4–8, an archwire slot recess 50 is provided to assist in aligning the bracket and to provide an area of reduced friction between the archwire (not shown) and archwire slot 24. As can be seen more clearly in FIGS. 6 and 8, archwire slot recess 50 has bottom surface 51 which is below bottom surface 52 of archwire slot 24. Archwire slot recess 50 also has an occlusal edge 53 and a gingival edge 54 that provide a wider slot area than provided by walls 55 of archwire slot 24. Thus, when the archwire, having a rectangular (or other) configuration, is received in archwire slot 24, it will generally contact sides 55 and bottom surface 52 of the archwire slot, and will not contact the recessed portion of the archwire slot recess 50, namely occlusal and gingival edges 53, 54. Accordingly, the friction generally arising between the archwire and the archwire slot is sufficiently reduced since there is less surface area in the archwire slot that is in direct contact with the archwire.

As an added advantage of archwire slot recess 50, the edges provide additional sight lines to assist in aligning the bracket with tooth long axis 15 and occlusal plane 10 when mounting the bracket on the tooth. Archwire slot recess 50 has a generally rhomboidal configuration with mesial and distal edges 56, 57 being parallel to each other and parallel to the tooth long axis. Similarly, occlusal edge 53 and gingival edge 54 are parallel to each other and parallel to occlusal plane 10. The various edges of archwire slot 50 provide consistent visual cues for assistance in aligning the bracket on the tooth.

It will be readily apparent to those skilled in the art that all of the aforementioned reference lines or sight lines provide consistent visual cues to assist the orthodontist in aligning the bracket on the tooth. It should be noted, that although the bracket depicted in FIGS. 4–8 has a generally rectangular configuration when viewed in the buccolabial view (facial view), the advantages of the present invention can be obtained with other bracket configurations as well.

Figure 9:
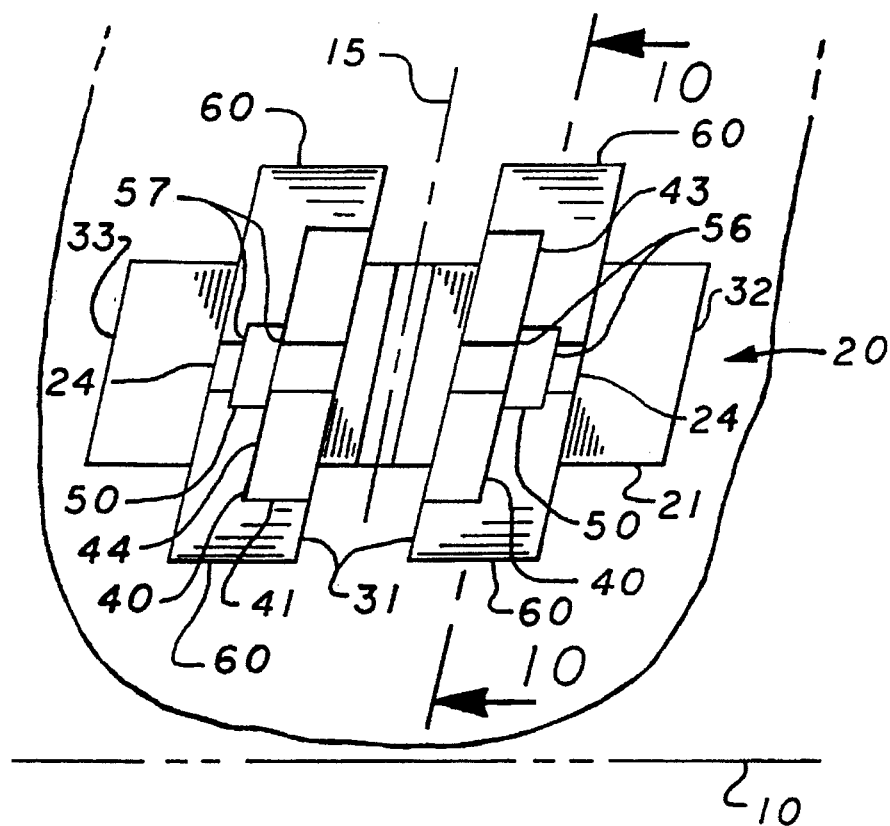
FIG. 9 is a front elevational view of another embodiment of the orthodontic bracket of the present invention.
Figure 10:
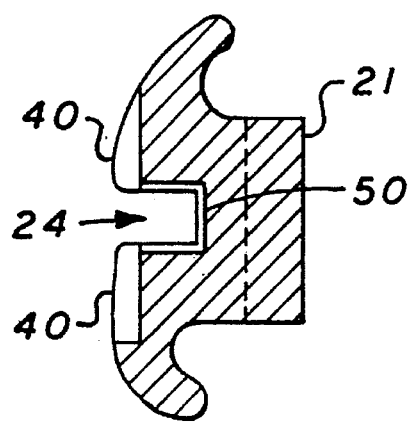
FIG. 10 is a cross-sectional view of FIG. 9 taken along lines 10—10.

For example, as depicted in FIGS. 9–11, a generally rhomboidal-shaped orthodontic bracket 5 has a tie wing recess 40 and an archwire slot recess 50, both of which are angulated to assist with the alignment of the bracket along the tooth long axis and occlusal plane. The rhomboidal-shaped bracket has the added advantage of tie wing tips 60 being parallel to each other, to archwire slot 24, and to occlusal plane 10.

The orthodontic brackets referred to in FIGS. 4–11 depict the invention embodied in a twin tie wing bracket, i.e. a bracket having a mesial and distal tie wing. Generally, it is felt that two tie wings can provide better rotational characteristics since they are spaced a distance apart. However, single wing tie wing brackets can also benefit from the present invention.

As an example of a single wing bracket incorporating the present invention, reference is made to FIG. 13 in which a single wing orthodontic bracket 70 is mounted on base pad 71. An archwire slot 72 is positioned in said single wing bracket 70 at an angle such that archwire slot 72 is parallel to occlusal plane 10. Archwire slot 72 has an occlusal edge 73 and a gingival edge 74, both of which are parallel to occlusal plane 10.

In keeping with the invention and referring to FIGS. 13 and 14, a tie wing recess 75 is formed in single wing bracket 70 such that the mesial edge 76 and the distal edge 78 of tie wing recess 75 are parallel to tooth long axis 15. Tie wing recess 75 also has an occlusal edge 79 and gingival edge 80, both of which are parallel to each other and parallel to occlusal plane 10. Thus, tie wing recess 75 has an overall appearance of that of a rhomboidal configuration which, as described with respect to the foregoing brackets, provides further sight lines which assist in aligning the bracket with respect to the tooth long axis and the occlusal plane.

Single wing bracket 70 also has an archwire recess 85 which includes mesial edge 86 and distal edge 87, both of which are parallel to each other and parallel to tooth long axis 15. Archwire slot recess 85 also has occlusal edge 88 and gingival edge 89 that are parallel to each other and parallel to occlusal plane 10. As best depicted in FIG. 14, archwire slot recess 85 has bottom surface 90 which is situated below bottom surface 92 of archwire slot 72 such that the archwire (not shown) does not come in contact with bottom surface 90. Archwire recess 85 also has occlusal surface 93 and gingival surface 94, both of which are recessed from the sides of archwire slot 72, again so that the archwire does not come into contact with occlusal surface 93 and gingival surface 94. Because of these recessed surfaces, there is less friction between the archwire and archwire slot 72 since archwire slot recess 85 is not in contact with the archwire.

As is clear to one skilled in the art, the overall configuration of the bracket may be rectangular, rhomboidal, trapezoidal, or any other geometric shape and still embody the scope and content of the invention having a rhomboidal-shaped tie wing recess and a rhomboidal-shaped archwire slot recess.

Those skilled in the art will also appreciate that the brackets of the present invention can be made from various materials including stainless steel, tantalum, ceramic, certain polymers, and generally any other orthodontic bracket material compatible with long-term residence in the mouth. It should also be understood that the brackets of the present invention can be formed by any of the known manufacturing methods which include casting, molding, machining, and the like. The method of manufacture, and the material composition of the bracket are not considered as forming the basis of the invention, and can be carried out by conventional methods.

As used herein, those skilled in the art will understand the term "occlusal plane" as the imaginary plane created by the occlusal edges of the teeth when the mouth is closed. The term "occlusal plane" has been used herein with such definition in mind, and also to refer to the occlusal edge of one tooth.

The tooth long axis has been used herein to refer to an imaginary line that runs generally from the apex of the tooth through the center of the tooth to the tooth root. Thus, it could be said that the tooth would rotate on its axis which is the tooth long axis.

While the invention has been described and illustrated herein in terms of its use as an orthodontic bracket having specific alignment features for alignment with the tooth long axis and occlusal plane, it will be clear that miner modifications and improvements may be made without departing from the scope of the invention. Thus, references to certain edges or surfaces as being "parallel" to the tooth long axis or occlusal plane are meant to be generally or substantially parallel to those reference lines. Further, it should be borne in mind that references to a rhomboidal or rectangular configuration is meant to be a generally rhomboidal or generally rectangular configuration given the tolerances involved during the manufacturing processes.

What is claimed is:

1. An orthodontic appliance for aligning with the occlusal plane and tooth long axis of a patient's tooth, comprising:

an orthodontic bracket having a mesial tie wing and a distal tie wing attached to a base pad;

an archwire slot disposed in said mesial tie wing and said distal tie wing such that said archwire slot is parallel to the occlusal plane of the patient's tooth when said orthodontic bracket is mounted on the tooth; and an archwire slot recess positioned in and passing partially through each of said mesial tie wing and said distal tie wing without passing through the outer edge of either tie wing, said archwire slot recess having at least an occlusal edge parallel to said archwire slot, wherein said archwire slot and said occlusal edge of said archwire slot recess facilitate alignment with the occlusal plane of the patient's tooth when said orthodontic bracket is mounted on the tooth.

2. The orthodontic bracket of claim 1, wherein said archwire slot recess has a gingival edge parallel to the archwire slot.

3. The orthodontic bracket of claim 1, wherein said archwire slot recess has a mesial edge and distal edge, said archwire slot recess mesial and distal edges each being parallel to the long axis of the patient's tooth when said orthodontic bracket is mounted on the tooth with said archwire slot parallel to the occlusal plane of the tooth.

4. The orthodontic bracket of claim 1, wherein said mesial tie wing and said distal tie wing each have an inner edge parallel to the tooth long axis when said orthodontic bracket is mounted on the tooth with said archwire slot parallel to the occlusal plane of the tooth.

5. The orthodontic bracket of claim 1, wherein said base pad has an occlusal edge parallel to said archwire slot.

6. The orthodontic bracket of claim 5, wherein said base pad has a mesial edge and a distal edge, said base pad mesial edge and said base pad distal edge each being parallel to the tooth long axis when said orthodontic bracket is mounted on the tooth with said archwire slot parallel to the occlusal plane of the tooth.

7. The orthodontic bracket of claim 1, wherein said mesial tie wing and said distal tie wing each have a substantially rectangular configuration.

8. The orthodontic bracket of claim 7, wherein said mesial tie wing and said distal tie wing each have a curved outer edge.

9. The orthodontic bracket of claim 1, wherein said mesial tie wing and said distal tie wing each have a substantially rhomboidal configuration.

10. The orthodontic bracket of claim 1, wherein said base pad has a groove spaced substantially equidistant between said mesial tie wing and said distal tie wing, said groove being substantially parallel to the tooth long axis when said orthodontic bracket is mounted on the tooth with said archwire slot parallel to the occlusal plane of the tooth.

11. An orthodontic appliance for aligning with the occlusal plane and tooth long axis of a patient's tooth comprising:

an orthodontic bracket having a mesial tie wing and a distal tie wing attached to a base pad;

an archwire slot disposed in said mesial tie wing and said distal tie wing such that said archwire slot is parallel to the occlusal plane of the patient's tooth when said bracket is mounted on a tooth;

a tie wing recess in said mesial tie wing and said distal tie wing, said tie wing recess overlying said archwire slot and having at least an occlusal edge parallel to said archwire slot; and an archwire slot recess having at least an occlusal edge parallel to said archwire slot, wherein said archwire slot and said occlusal edge of said archwire slot recess and said occlusal edge of said tie wing recess facilitate alignment with the occlusal plane of the patient's tooth when said orthodontic bracket is mounted on the tooth.

12. The orthodontic bracket of claim 11, wherein said tie wing recess and said archwire slot recess each have a gingival edge parallel to said archwire slot.

13. The orthodontic bracket of claim 11, wherein said tie wing recess and said archwire slot recess each have a mesial edge and a distal edge, each of said tie wing recess mesial and distal edges and said archwire slot recess distal and mesial edges being parallel to the long axis of the patient's tooth when said orthodontic bracket is mounted on the tooth with said archwire slot parallel to the occlusal plane of the tooth.

14. The orthodontic bracket of claim 11, wherein said mesial tie wing and said distal tie wing each have an inner edge parallel to the tooth long axis.

15. The orthodontic bracket of claim 11, wherein said base pad has an occlusal edge parallel to said archwire slot.

16. The orthodontic bracket of claim 15, wherein said base pad has a mesial edge and a distal edge, said base pad mesial edge and said base pad distal edge each being parallel to the tooth long axis when said orthodontic bracket is mounted on the tooth with said archwire slot parallel to the occlusal plane of the tooth.

17. The orthodontic bracket of claim 11, wherein said mesial tie wing and said distal tie wing each have a substantially rectangular configuration.

18. The orthodontic bracket of claim 17, wherein said mesial tie wing and said distal tie wing each have a curved outer edge.

19. The orthodontic bracket of claim 11, wherein said mesial tie wing and said distal tie wing each have a substantially rhomboidal configuration.

20. The orthodontic bracket of claim 11, wherein said base pad has a groove spaced substantially equidistant between said mesial tie wing and said distal tie wing, said groove being substantially parallel to the tooth long axis.

21. The orthodontic bracket of claim 11, wherein said mesial tie wing and said distal tie wing each have a substantially trapezoidal configuration.

22. An orthodontic appliance for aligning with the occlusal plane and the tooth long axis of a patient's tooth, comprising:

an orthodontic bracket having a mesial tie wing and a distal tie wing attached to a base pad, said mesial tie wing and said distal tie wing each having an outer edge;

an archwire slot disposed in said mesial tie wing and said distal tie wing such that said archwire slot is parallel to the occlusal plane of a patient's tooth when said orthodontic bracket is mounted on the tooth; and a tie wing recess in said mesial tie wing and said distal tie wing, said tie wing recess having at least an occlusal edge parallel to said archwire slot, wherein said archwire slot and said occlusal edge of said tie wing recess facilitate alignment with the occlusal plane of the patient's tooth when said orthodontic bracket is mounted on the tooth, said tie wing recess further having a mesial edge and a distal edge, said mesial edge and said distal edge positioned inward of the outer edges of each tie wing, said mesial edge and said distal edge further being parallel to the long axis of the patient's tooth when said orthodontic bracket is mounted on the tooth with said archwire slot parallel to the occlusal plane of the tooth.

23. The orthodontic bracket of claim 22, wherein said tie wing recess has a gingival edge parallel to said archwire slot.

24. The orthodontic bracket of claim 22, wherein said mesial tie wing and said distal tie wing each have an inner edge parallel to the tooth long axis when said orthodontic bracket is mounted on the tooth with said archwire slot parallel to the occlusal plane of the tooth.

25. The orthodontic bracket of claim 22, wherein said base pad has an occlusal edge parallel to said archwire slot.

26. The orthodontic bracket of claim 25, wherein said base pad has a mesial edge and a distal edge, said base pad mesial and distal edge each being parallel to the tooth long axis when said orthodontic bracket is mounted on the tooth with said archwire slot parallel to the occlusal plane of the tooth.

27. The orthodontic bracket of claim 22, wherein said mesial tie wing and said distal tie wing each have a substantially rectangular configuration.

28. The orthodontic bracket of claim 27, wherein said mesial tie wing and said distal tie wing each have a curved outer edge.

29. The orthodontic bracket of claim 22, wherein said base pad has a groove spaced substantially eguidistant between said mesial tie wing and said distal tie wing, said groove being substantially parallel to the tooth long axis when said orthodontic bracket is mounted on the tooth with said archwire slot parallel to the occlusal plane of the tooth.

30. The orthodontic bracket of claim 22, wherein said mesial tie wing and said distal tie wing each have a substantially rhomboidal configuration.

31. An orthodontic appliance for aligning with the occlusal plane and the tooth long axis of a patient's tooth, comprising:

an orthodontic bracket having a mesial tie wing and a distal tie wing attached to a base pad:

said base pad having a grooved space substantially equidistant between said mesial tie wing and said distal tie wing, said groove being substantially parallel to the tooth-long axis;

an archwire slot disposed in said mesial tie wing and said distal tie wing such that said archwire slot is parallel to the occlusal plane of a patient's tooth;

a tie wing recess in said mesial tie wing and said distal tie wing, said tie wing recess having at least an occlusal edge parallel to said archwire slot, wherein said archwire slot and said occlusal edge of said tie wing recess facilitate alignment with the occlusal plane of the patient's tooth when said orthodontic bracket is mounted on the tooth.

* * * * *